(12) United States Patent
Kirschman

(10) Patent No.: US 11,596,892 B2
(45) Date of Patent: *Mar. 7, 2023

(54) SYSTEM AND METHOD FOR MAINTAINING, MONITORING AND/OR IMPROVING AIR QUALITY AND PURITY IN AT LEAST ONE ROOM OR ENVIRONMENT

(71) Applicant: David Louis Kirschman, Dayton, OH (US)

(72) Inventor: David Louis Kirschman, Dayton, OH (US)

(73) Assignee: Aerobiotix, LLC, Miamisburg, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 17/404,265

(22) Filed: Aug. 17, 2021

(65) Prior Publication Data

US 2021/0370217 A1 Dec. 2, 2021

Related U.S. Application Data

(63) Continuation of application No. 15/923,096, filed on Mar. 16, 2018, now Pat. No. 11,123,674.

(Continued)

(51) Int. Cl.
*B01D 46/00* (2022.01)
*B01D 46/44* (2006.01)
(Continued)

(52) U.S. Cl.
CPC ............. *B01D 46/46* (2013.01); *A61L 9/20* (2013.01); *B01D 46/0032* (2013.01); *B01D 46/442* (2013.01); *B01D 46/446* (2013.01); *B01D 46/448* (2013.01); *B01D 46/88* (2022.01); *F24F 3/16* (2013.01); *F24F 11/30* (2018.01); *G06Q 10/087* (2013.01); *G16H 40/20* (2018.01); *G16H 40/40* (2018.01); *G16H 40/63* (2018.01); *A61G 10/02* (2013.01); *A61L 9/22* (2013.01); *A61L 2209/111* (2013.01); *A61L 2209/12* (2013.01); *A61L 2209/14* (2013.01);

(Continued)

(58) Field of Classification Search
CPC .. B01D 46/46; B01D 46/0032; B01D 46/008; B01D 46/442; B01D 46/446; G16H 40/63; G16H 40/40; G16H 40/20; F24F 3/16; F24F 11/30; F24F 2110/50; A61L 9/20; A61L 2209/111; A61L 2209/14; G06Q 10/087
USPC ...... 55/385.1, 472, 473, DIG. 34; 95/25, 26; 96/417, 422, 424, 397
See application file for complete search history.

(56) References Cited

U.S. PATENT DOCUMENTS

| | | |
|---|---|---|
| 3,721,067 A | 3/1973 | Agnew |
| 3,966,407 A | 6/1976 | Zuckerberg et al. |

(Continued)

FOREIGN PATENT DOCUMENTS

| | | |
|---|---|---|
| WO | 2010/063867 | 6/2010 |
| WO | WO 2010/063867 | 6/2010 |

(Continued)

*Primary Examiner* — Minh Chau T Pham
(74) *Attorney, Agent, or Firm* — Jacox, Meckstroth & Jenkins

(57) ABSTRACT

A system and method for maintaining, monitoring and improving air quality and purity in a room or environment, such as a hospital room or operating room.

48 Claims, 3 Drawing Sheets

Related U.S. Application Data

(60) Provisional application No. 62/472,822, filed on Mar. 17, 2017.

(51) Int. Cl.

| | | |
|---|---|---|
| *B01D 46/88* | (2022.01) | |
| *F24F 3/16* | (2021.01) | |
| *F24F 11/30* | (2018.01) | |
| *A61L 9/22* | (2006.01) | |
| *B01D 46/46* | (2006.01) | |
| *A61L 9/20* | (2006.01) | |
| *G16H 40/63* | (2018.01) | |
| *G16H 40/40* | (2018.01) | |
| *G16H 40/20* | (2018.01) | |
| *G06Q 10/087* | (2023.01) | |
| *F24F 110/50* | (2018.01) | |
| *A61G 10/02* | (2006.01) | |

(52) U.S. Cl.
CPC ....... *A61L 2209/16* (2013.01); *A61L 2209/21* (2013.01); *B01D 2279/51* (2013.01); *F24F 2110/50* (2018.01)

(56) References Cited

U.S. PATENT DOCUMENTS

| | | |
|---|---|---|
| 3,998,142 A | 12/1976 | Foreman et al. |
| 4,600,557 A | 7/1986 | Spitz |
| 4,781,108 A | 11/1988 | Nillson |
| 5,086,692 A | 2/1992 | Welch et al. |
| 6,045,596 A | 4/2000 | Holland, Jr. et al. |
| 7,617,137 B2 | 11/2009 | Kreiner et al. |
| 7,686,872 B2 | 3/2010 | Kang |
| 7,761,188 B2 | 7/2010 | Palmerton et al. |
| 7,774,244 B2 | 8/2010 | Kreiner et al. |
| 7,996,286 B2 | 8/2011 | Kreiner et al. |
| 8,781,920 B2 | 7/2014 | Kreiner et al. |
| 9,070,270 B2 | 6/2015 | Kreiner et al. |
| 9,433,693 B2 | 9/2016 | Kirschman |
| 9,457,119 B2 | 10/2016 | Kirschman |
| 9,764,054 B2 | 9/2017 | Kirschman |
| 9,883,980 B2 | 2/2018 | Lapuente |
| 10,188,976 B2 | 1/2019 | Cho et al. |
| 10,219,750 B2 * | 3/2019 | Duan ................. B60H 3/02 |
| 10,222,077 B2 | 3/2019 | Takei et al. |
| 10,663,184 B2 | 5/2020 | Park et al. |
| 10,695,706 B2 | 6/2020 | Cho et al. |
| 11,123,674 B2 * | 9/2021 | Kirschman ........... B01D 46/88 |
| 2005/0258961 A1 | 11/2005 | Kimball et al. |
| 2007/0186777 A1 | 8/2007 | Ting |
| 2008/0147529 A1 | 6/2008 | Kreiner et al. |
| 2010/0017224 A1 | 1/2010 | Kreiner et al. |
| 2010/0262433 A1 | 10/2010 | Kreiner et al. |
| 2011/0230130 A1 | 9/2011 | Ruizlapuente |
| 2012/0031271 A1 | 2/2012 | Haslebacher |
| 2012/0136674 A1 | 5/2012 | Kreiner et al. |
| 2014/0157989 A1 | 6/2014 | Kirschman |
| 2014/0324643 A1 | 10/2014 | Kreiner et al. |
| 2015/0088786 A1 | 3/2015 | Anandhakrishnan |
| 2015/0302492 A1 | 10/2015 | Kreiner et al. |
| 2016/0263267 A1 | 9/2016 | Kirschman |
| 2017/0296691 A1 | 10/2017 | Kirschman |

FOREIGN PATENT DOCUMENTS

| | | |
|---|---|---|
| WO | WO 2014/106738 | 7/2014 |
| WO | 2014/106738 | 7/2017 |

* cited by examiner

SYSTEM AND METHOD FOR MAINTAINING, MONITORING AND/OR IMPROVING AIR QUALITY AND PURITY IN AT LEAST ONE ROOM OR ENVIRONMENT

CROSS-REFERENCE TO RELATED APPLICATION

The present application is a continuation of U.S. application Ser. No. 15/923,096 filed Mar. 16, 2018, now U.S. Pat. No. 11,123,674 B2 which claims priority to provisional U.S. Application Ser. No. 62/472,822, filed Mar. 17, 2017, to which Applicant claims the benefit of the earlier filing date. These applications are incorporated herein by reference and made a part hereof.

BACKGROUND OF THE INVENTION

1. Field of the Invention

This invention relates to a system and method for maintaining, monitoring and improving air quality and purity in a room or environment, such as a hospital room or operating room.

2. Description of the Related Art

The increasing prevalence of drug resistant pathogens has increased interest in environmental elimination of pathogens, particularly in health care settings. Several inventions have made claims to eliminating pathogens in these settings. One area of concern is the operating room, where surgical site infections have led to significant human and economic costs. Typically, air quality in operating room settings has relied on fixed ventilation systems which provide various rates of air exchange and positive room pressure. However, such systems may not be adequate for evolving needs of surgical procedures. High room traffic, equipment, and multiple procedure turnovers per day have increased airborne bioload, necessitating additional air purification capacity in many operating rooms. This is particularly true with the increased use of surgical implants, which are susceptible to bacterial colonization.

The use of portable HEPA filters and recirculating devices in the operating room has been described. However, these units are not appropriate for operating room use because the units and/or their intake filters can become contaminated with infectious biological debris. This can spread contamination from one procedure to the next.

Another problem with the prior art is the collection, assimilation and understanding of data associated with a patient, the patient's associated clinical data and the actual physical parameters of the operating room in which the patient may undergo a procedure. In the past, an operating room was typically scheduled and used without measurements of air contamination or evaluation of the physical data associated with the operating room, the patient and the air quality in the operating room.

Still another problem with the prior art is that very little, if any, research and information could be gathered or conducted which compared or correlated air quality and contamination levels in a room, such as an operating room, with information relating to at least one or a plurality of patients so that correlations could be made between, for example, infection rates of patients who underwent a common surgical procedure.

What is therefore needed is a method to purify operating room air which allows each surgical procedure to have a non-contaminated air purifier to prevent the spread of bacterial contamination.

SUMMARY OF THE INVENTION

It is, therefore, one object of the invention to provide a system and method for improving air quality in a room or environment, such as a hospital room or operating room.

Another object of the invention is to provide a system and method which is adapted to gather and collect clinical and physical data and parameters associated with a patient and also physical data and parameters associated with at least one room or environment where the patient is located.

Another object of the invention is to provide a system and method for collecting information for evaluation and study in order to improve air quality in a room or environment.

Still another object of the invention is to provide a system and method that either automatically or manually evaluates and/or correlates patient data with physical data and parameters for a room or environment and performs at least one or a plurality of actions in response thereto.

Still another object of the invention is to provide for an inventory and data collection system that is adapted to evaluate at least one of clinical and physical data and parameters for a patient and physical data and parameters for a room, such as an operating room and form at least one or a plurality of the following actions:

Research (e.g., infection rates versus room air quality)
Air quality control
Room contamination evaluation and remediation
Air purifier monitoring
Air cleaning element quality
Air cleaning element reorder
Air cleaning element replacement
Air cleaning element cleaning
Room condition sensing
  Temperature
  Humidity
  Air quality
Record retention of air quality and room conditions
Alarm
Investigation of issues Yet another object of the invention is to provide a system and method for automatically reordering at least one cleaning element in response to at least one of clinical and physical data and parameters associated with a patient or physical data and parameters associated with a room.

Yet another object of the invention is to provide a system and method that correlates air quality in a room or environment with clinical data, such as clinical procedure and/or infection rates.

Another object of the invention is to provide a system and method that gives a complete picture of clinical and physical data for a patient and room, respectively, and identifies areas of concern or issues.

In one aspect, one embodiment of the invention comprises a system for maintaining or monitoring at least one environment having at least one air purifier, the system comprising at least one first input or input means for a user to input at least one of clinical data or physical parameters into a collection system, at least one second input or sensor associated with the environment for collecting physical data regarding the environment and for inputting it into the collection system, at least one output for outputting the at least one of clinical or physical parameters and the physical data, at least one element that uses and processes the at least one of clinical or physical parameters and the physical data in a predetermined format as input from the at least one first input and the at least one second input, respectively, and outputs integrated information, and the system being adapted to permit a user to use such integrated information to at least one of maintain or improve the at least one of the environment or take at least one action in response to the integrated information, the integrated information being adapted or used for at least one of research, improving air quality, quality review of the environment or control or notification of at least one issue associated with the environment or the integrated information.

In another aspect, another embodiment of the invention comprises a system for improving air quality in at least one hospital room or operating room, the system comprising at least one first input or sensor for inputting for a user to input at least one of clinical data or physical parameters into a collection system, at least one second input or sensor associated with an environment for collecting physical data regarding the environment and for inputting it into the collection system, at least one output for outputting the at least one of clinical or physical parameters and the physical data, at least one element that uses and processes the at least one of clinical or physical parameters and the physical data as input from the at least one first input and the at least one second input, respectively, and outputs integrated information, and the system being adapted to permit use of such integrated information to take at least one action that at least one of maintains or improves the air quality.

In still another aspect, another embodiment of the invention comprises a method for maintaining or monitoring at least one environment having at least one air purifier, the method comprising the steps of inputting at least one clinical data or physical parameters into a collection system, sensing physical data regarding the at least one environment and for inputting it into the collection system, outputting from the collection system at least one output generated using the at least one of clinical or physical parameters and the physical data, using at least one element to process the at least one of clinical or physical parameters and the physical data as input from at least one first input and at least one second input, respectively, and outputs integrated information in response thereto, and using such integrated information to at least one of maintain or improve the at least one of the environment or take at least one action in response to the integrated information, the integrated information being adapted or used for at least one of research, improving air quality, quality review of the environment or control or notification of at least one issue associated with the environment or the integrated information.

In still another aspect, another embodiment of the invention comprises an inventory system for supporting the purifying of operating room air on a per-patient basis consisting of a record of patient identifying information, a record describing an air cleaning element utilized in an air purifier located in an operating room, the air cleaning element being used for an individual patient procedure, the record describing the air cleaning element comprising manufacturer name, part number, and/or serial number in association with the patient identifying information, the inventory system adapted to facilitate inventory actions such as re-ordering, replacement, recordkeeping, invoicing and/or billing of the air cleaning element, the inventory system associating the inventory actions to the patient identifying information.

In still another aspect, another embodiment of the invention comprises a method of purifying operating room air comprising activating a portable air purifier, after a surgical procedure, removing a contaminated air cleaning element from the air purifier, recording data regarding the air cleaning element to effect remuneration or recordkeeping by hospital, air cleaning element manufacturer, patient, or related payor in electronic or paper medical record or related document, replacing the air cleaning element with new air cleaning element.

In still another aspect, another embodiment of the invention comprises a method of purifying operating room air comprising locating an area of an operating room which has the highest amount of human traffic/and or airborne contamination, positioning an air purifier proximate to the area, the air purifier having an air cleaning element, after a surgical procedure, removing a contaminated air cleaning element from the air purifier, recording data regarding the air cleaning element to effect remuneration or recordkeeping by hospital, air cleaning element manufacturer, patient, or related payor in electronic or paper medical record or related document, replacing the air cleaning element with a new air cleaning element.

In still another aspect, another embodiment of the invention comprises a method of purifying operating room air comprising positioning an air purifier adjacent to an operating room door, instrument table or patient table, the air purifier having an air cleaning element, after a surgical procedure, removing a contaminated air cleaning element from the air purifier, recording data regarding the air cleaning element to effect remuneration or recordkeeping by hospital, air cleaning element manufacturer, patient, or related payor in electronic or paper medical record or related document, replacing the air cleaning element with new air cleaning element.

In still another aspect, another embodiment of the invention comprises a method of purifying operating room air comprising placing an air purifier, the air purifier having means for direct bacterial deactivation, such as irradiation, chemical oxidation, or ionization, and an air cleaning element, after a surgical procedure, removing a contaminated air cleaning element from the air purifier, recording data regarding the air cleaning element to effect remuneration or recordkeeping by hospital, air cleaning element manufacturer, patient, or related payor in electronic or paper medical record or related document, replacing the air cleaning element with new air cleaning element.

In still another aspect, another embodiment of the invention comprises a method of purifying operating room air comprising placing an air purifier, the air purifier having means for air quality monitoring and an air cleaning element, after a surgical procedure, removing a contaminated air cleaning element from the air purifier, recording data regarding the air cleaning element to effect remuneration or recordkeeping by hospital, air cleaning element manufacturer, patient, or related payor in electronic or paper medical record or related document, recording data regarding air quality information in a patient record or related record, replacing the air cleaning element with new air cleaning element.

In still another aspect, another embodiment of the invention comprises a method for providing an air purifier for operating room use, the purifier provided to the hospital or surgical facility at no cost or for materially less than the typical purchase cost of comparable product, the purifier containing an interchangeable air cleaning element, the air cleaning element changed on a per patient basis, the hospital or surgical facility, patient, payor or related party, paying for the air cleaning element on a per-patient basis, revenue from the air cleaning element usage offsetting cost of the purifier.

In still another aspect, another embodiment of the invention comprises an inventory and data collection system, operative with an air purification device, for the purpose of recording and integration of data regarding physical parameters and clinical parameters within a clinical situation.

This invention, including all embodiments shown and described herein, could be used alone or together and/or in combination with one or more of the features covered by one or more of the following list of features:

The system wherein the at least one action is a service of the air purifier.
The system wherein the service is changing an air cleaning element in the air purifier.
The system wherein the at least one action is automatically controlling operation of the air purifier in the at least one environment in response to the integrated information.
The system wherein the at least one action is using the integrated information for at least one of research, evaluation of air particulate levels, or providing a condition of the at least one environment.
The system wherein the condition of the at least one environment is at least one of air particulate level, contamination level, cleanliness, temperature, humidity or air quality.
The system wherein the at least one environment is a room where a patient is located.
The system wherein the at least one environment is an operating room.
The system wherein the clinical data is at least one of patient information and/or identification codes, diagnosis, location identification, clinical event type, clinical event length or clinical event time.
The system wherein the physical data is at least one of air particulate levels, air quality, temperature, humidity, air purifier functionality, ultraviolet output, air cleaning element condition, air cleaning element identification codes or air purifier identification codes.
The system wherein the at least one action is a service of an air purifier.
The system wherein the service is re-ordering a replacement air cleaning element for the air purifier.
The system wherein the service is changing an air cleaning element in the air purifier.
The system wherein the at least one action is automatically controlling operation of an air purifier in the at least one hospital room or operating room in response to the integrated information.
The system wherein the at least one action is using the integrated information for at least one of research, evaluation of air particulate levels, or providing a condition of the at least one hospital room or operating room.
The system wherein the condition of the at least one hospital room or operating room is at least one of air particulate level, contamination level, cleanliness, temperature, humidity or air quality.
The system wherein the clinical data is at least one of patient information and/or identification codes, diagnosis, location identification, clinical event type, clinical event length or clinical event time.
The system wherein the physical data is at least one of air particulate levels, air quality, temperature, humidity, air purifier functionality, ultraviolet output, air cleaning element condition, air cleaning element identification codes or air purifier identification codes.
The system wherein said at least one action includes at least one of research, air quality control, room contamination evaluation and remediation, air purifier monitoring, air cleaning element quality, air cleaning element reorder, air cleaning element replacement, air cleaning element cleaning, room condition sensing temperature, humidity and/or air quality, record retention of air quality and room conditions, alarm and/or investigation of issues.
The system wherein the at least one sensor comprises at least one of an air particle sensor, an optical sensor, an internal pressure sensor, a humidity sensory and/or a temperature sensor.
The system wherein the air cleaning element may be one of an air filter, an electrostatic screen, an ultraviolet light or the like.
The method wherein the at least one action is a service of the air purifier.
The method wherein the method comprises the step of changing an air cleaning element in the air purifier in response to the integrated information.
The method wherein the method further comprises the step of automatically controlling operation of the air purifier in the at least one environment in response to the integrated information.
The method wherein the method further comprises the step of using the integrated information for at least one of research, evaluation of air particulate levels, or providing a condition of the at least one environment.
The method wherein the condition of the at least one environment is at least one of air particulate level, contamination level, cleanliness, temperature, humidity or air quality.
The method wherein the at least one environment is a room where a patient is located.
The method wherein the at least one environment is an operating room.
The method wherein the clinical data is at least one of patient information and/or identification codes, diagnosis, location identification, clinical event type, clinical event length or clinical event time.
The method wherein the physical data is at least one of air particulate levels, air quality, temperature, humidity, air purifier functionality, ultraviolet output, air cleaning element condition, air cleaning element identification codes or air purifier identification codes.
The inventory and data collection system wherein the clinical situation is a surgical procedure.
The inventory and data collection system wherein the clinical parameters include at least one of patient information and/or identification codes, diagnosis, location identification, clinical event type, clinical event length, clinical event time.
The inventory and data collection system wherein the physical parameters include at least one of air particulate levels, air quality, temperature, humidity, air purifier functionality, ultraviolet output, air cleaning element condition, air cleaning element identification codes or air purifier identification codes.
The inventory and data collection system wherein the integration comprises a means to record and/or display the clinical and physical parameters substantially contemporaneously to allow for a user to readily evaluate the relationship between the parameters.

The inventory and data collection system wherein the system incorporates an input means to allow for automatic and/or user input of the clinical and physical parameters, the input means incorporating at least one of sensors, keyboard, touchscreen, remote signal, radiofrequency identification, or similar means.

The inventory and data collection system wherein the system incorporates an output means to allow for user monitoring of the clinical and physical parameters, the output means consisting of visual, printed, or electronic outputs for local or remote monitoring.

The inventory and data collection system wherein the system incorporates a storage means to allow for storage of the clinical and physical parameters, the storage means consisting of magnetic, solid state, cloud, or other equivalent data storage methodologies operating at a local or remote location.

These and other objects and advantages of the invention will be apparent from the following description, the accompanying drawings and the appended claims.

BRIEF DESCRIPTION OF THE ACCOMPANYING DRAWINGS

DETAILED DESCRIPTION OF THE PREFERRED EMBODIMENTS

Figure 1:
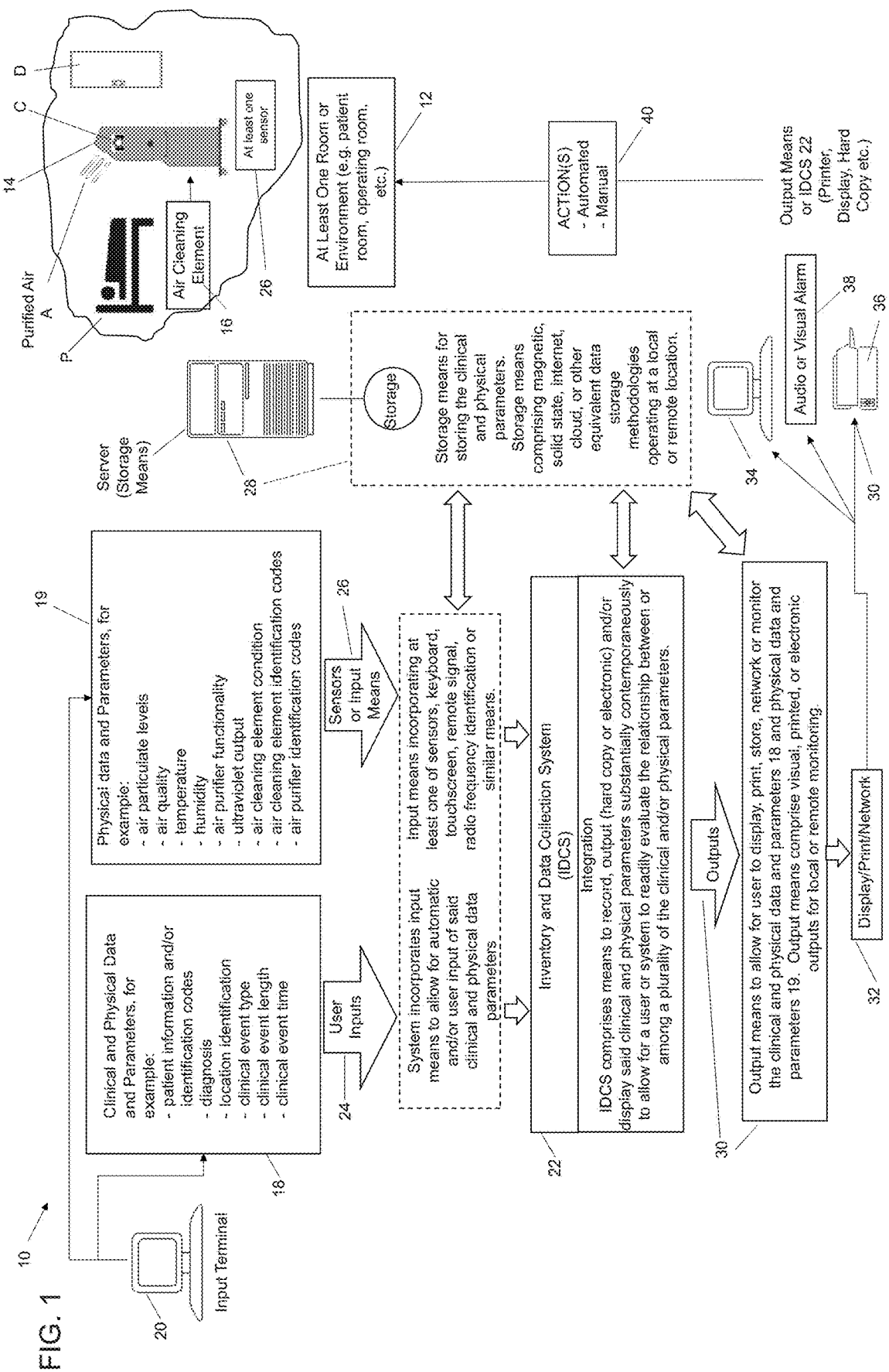
FIG. 1 is a view of a system in accordance with one embodiment of the invention.
Figure 2:
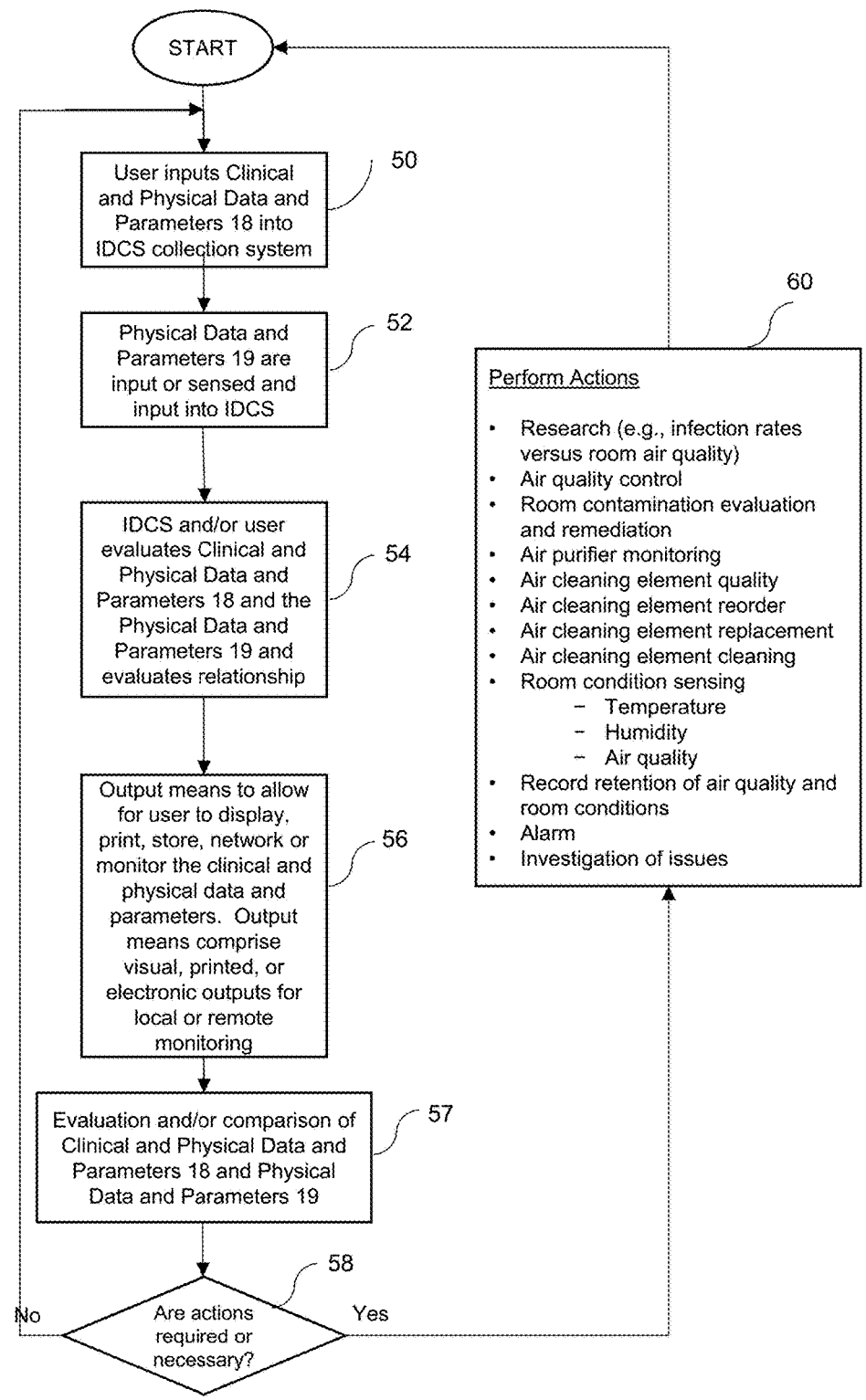
FIG. 2 is a schematic diagram of the process or method in accordance with an embodiment of the invention.

Referring now to FIGS. 1 and 2, a system 10 and method for maintaining, monitoring and improving air quality and purity in at least one room or environment 12 is shown. As a general overview, the system 10 and method being described is adapted and/or used in association with the at least one room or environment 12. In one embodiment, the at least one room or environment 12 is a room in a hospital, such as a patient room or an operating room where a patient P is located. As mentioned earlier, one object or goal of the invention is to maintain, monitor and/or improve the air quality in the at least one room or environment 12.

In the illustration being described, the system 10 comprises an air purifier 14 of the type available from Aerobiotix, Inc. of Dayton, Ohio. One or more of the air purifiers or features of the air purifiers shown in the following U.S. patents, which are owned by the Assignee of the present application, all of which are incorporated herein by reference and made a part hereof, may be used or adapted for use in the system 10: U.S. Pat. Nos. 9,433,693; 9,457,119; 9,764,054 and U.S. Patent Publication Nos. 2016/0263267 and 2017/0296691. The air purifier 14 comprises a replaceable air filter or air cleaning element 16. The air cleaning element 16 may be a Model No. PL-1 available from Aerobiotix, Inc. of Dayton, Ohio. It should be understood that the air cleaning element 16 may be an air filter, an electrostatic screen, an ultraviolet light, or the like.

In general, it is desirable to replace the air cleaning element 16 after it has been exposed to airborne contaminants in the air purifier 14, especially before a surgical or other procedure. For example, it is desirable not to replace the air cleaning element 16 prematurely (e.g., when it is not contaminated or dirty) or early in order to avoid the cost, and it is also desirable not to replace the air cleaning element too late when it becomes less effective with filtering airborne contaminants that pass through the air purifier 14. The air cleaning element 16 may be replaced based upon one or more variables, which may include time elapsed or number of procedures performed. The system 10 may comprise an internal clock (not shown) which is reset upon the air cleaning element 16 being changed or entry of specific procedures into the system 10 by a user. It should be understood that an air pressure sensor (not shown) associated with the air purifier 14 may also be used to measure increases in pressure which correlate to air cleaning element contamination. In general, the air purifier 14 is near a door D in the at least one room or environment 12 where the air purifier 14 is coupled to a power source and operated in the at least one room or environment 12 in order to purify the air therein.

As will be described later herein, one advantage of the system 10 and method described herein is that it is adapted to maintain, monitor and improve the air quality by automatically reordering the air cleaning element 16, suggested actions such as air cleaning element cleaning, air cleaning element replacement or providing information that will permit a user to order and/or replace the air cleaning element 16 in a timely manner.

Advantageously, the system 10 and method is adapted to collect clinical and physical data and parameters 18 which will be described in more detail later herein. The system 10 also generates physical data and parameters 19 associated with the at least one room or environment 12. The clinical and physical data and parameters 18 are illustrated in FIG. 1 and include various parameters or information relating to the patient P or procedure, such as patient information and/or identification codes associated with the patient P, a patient's diagnosis and/or patient location identification (e.g., if the patient in a patient room or in an operating room). The clinical and physical data and parameters 18 further include the clinical event type, such as a brain surgery, open heart surgery or other procedure. The clinical and physical data and parameters 18 further comprise clinical event length and clinical event time associated with the clinical event type.

In the illustration being described, the system 10 is adapted to receive that information from at least one input terminal 20 that a user may use to input the clinical and physical data and parameters 18 into an inventory and data collection system (IDCS) 22. The input terminal 20 provides input means 24 for inputting the clinical and physical data and parameters 18 to allow for automatic and/or user input of the clinical and physical data and parameters 18.

Figure 3:
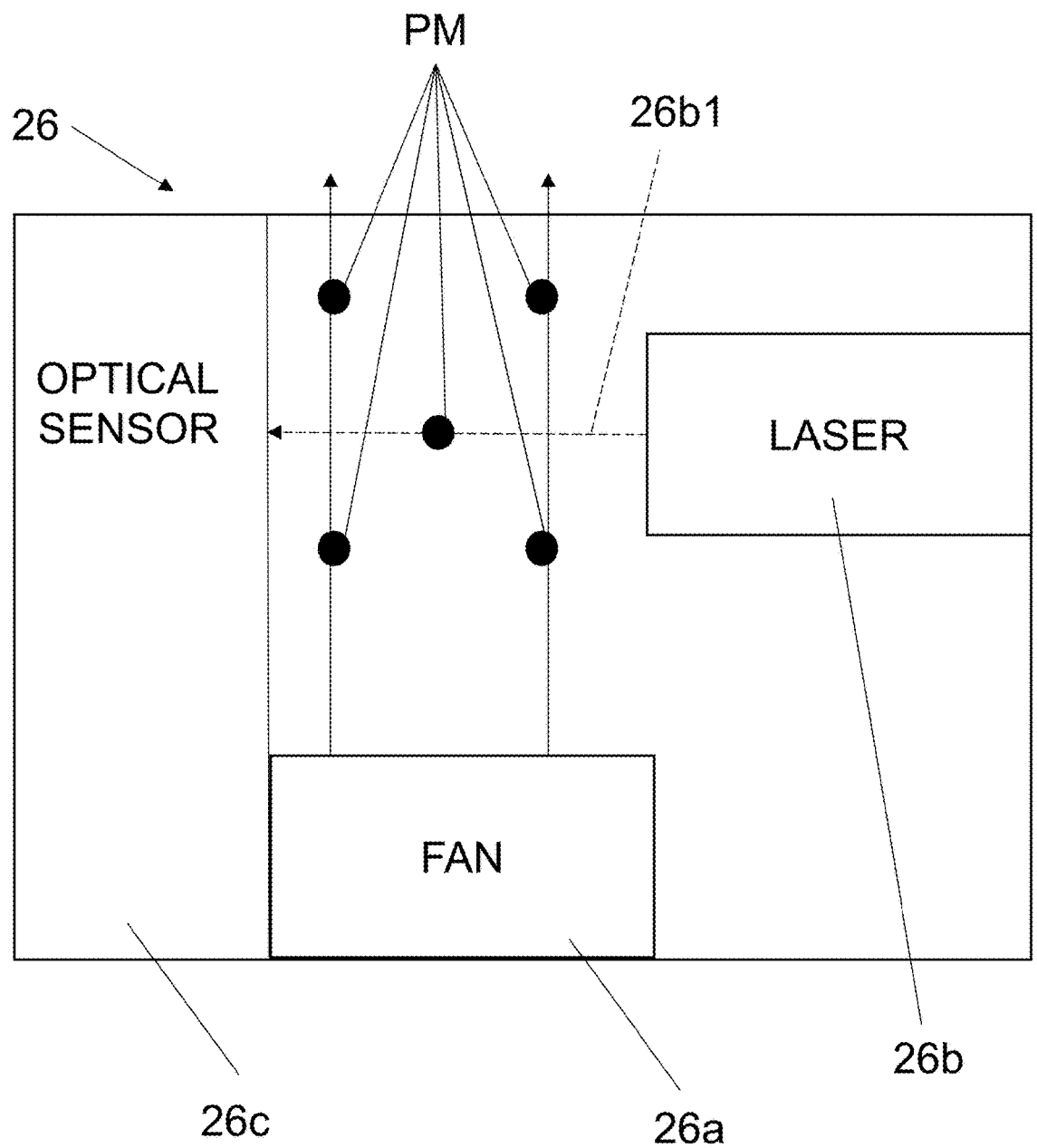
FIG. 3 is a schematic view of an air particulate sensor in accordance with one embodiment of the invention.

The system 10 and method are also adapted for generating, sensing and receiving the physical data and parameters 19 associated with the at least one room or environment 12. In the illustration being described, the physical data and parameters 19 include, for example, air particulate levels in the at least one room or environment 12, air quality, temperature, humidity, air purifier functionality, ultraviolet output, air cleaning element condition, air cleaning element identification codes, air purifier identification codes or other information regarding either the air purifier 14 or the at least one room or environment 12. The physical data and parameters 19 are generated by at least one or a plurality of sensors 26 associated with at least one of the air purifier 14 and the at least one room or environment 12. The at least one or a plurality of sensors 26 may comprise an air particulate sensor (FIG. 3) which measures the count or mass of particulates in the at least one room or environment 12. In the most common embodiment, the at least one or a plurality of sensors 26 contains a small fan 26a to draw in air and a low-power laser 26*b* that generates a beam 26*b*1 which is interrupted by particulate matter PM. The amount of laser interruption is detected by an optical sensor 26*c*, and air particulate levels are calculated in a manner conventionally known.

Contamination of the air cleaning element 16 can also be detected by an internal pressure sensor (not shown) in the air purifier 14. If the air cleaning element 16 becomes obstructed with debris, internal pressures will rise which can be logged by the system 10.

For example, a humidity and temperature sensor may be used to provide a temperature and humidity measurement. The system 10 may also comprise the least one or a plurality of sensors 26 associated with the air purifier 14 and adapted to provide sensed information regarding the air purifier 14. For example, the sensed information may include whether or not the air purifier 14 is functioning properly, the ultraviolet output of the air purifier 14, a level of contamination of the air cleaning element 16 and an air cleaning element identification code and/or an air purifier identification code which can help in maintaining the air purifier 14 and/or replacing one or more air cleaning elements 16 or other components of the air purifier 14.

Advantageously, the at least one sensor 26 may comprise an air particulate sensor for sensing the particulates and contamination in the air in the at least one room or environment 12. It should also be understood that these inputs may be user generated and input into the inventory and data collection system 22 using at least one or a plurality of terminals, such as the input terminal 20 illustrated in FIG. 1. The at least one sensor 26 or the input means or input terminal 20 may incorporate at least one of sensors, keyboard, touch screen, remote signal, radio frequency identification or similar means adapted to create, sense or input the physical data and parameters 19 into the inventory and data collection system 22.

Note that the system 10 further comprises data storage or storage means 28, such as a server, for storing the clinical and physical data and parameters 18 as well as the physical data and parameters 19 and outputs. In the illustration being described, the storage means 28 could comprise magnetic, solid state, cloud storage, such as on a server over the internet, or other equivalent data storage methodologies that may be operating at the location where the at least one room or environment 12 is located or could be at a remote location. It should be understood that the various inputs, the user input of the clinical and physical data and parameters 18 or sensed inputs of the physical data and parameters 19, are either sensed by the at least one sensor 26 or otherwise input into the system 10 and stored on the storage means 28.

Advantageously, the inventory and data collection system (IDCS) 22 comprises means to record, output (hard copy or electronic) and/or display the clinical and physical data and parameters 18 as well as the physical data and parameters 19 substantially contemporaneously to, for example, allow for a user or system to readily evaluate the relationship between or among a plurality of the clinical and physical data and parameters 18 and/or the physical data and parameters 19. The inventory and data collection system 22 is adapted to output data via an output or output means 30 to allow for a user to display, print, store, network or monitor the clinical and physical data and parameters 18 as well as the physical data and parameters 19. In the illustration being described, the output means 30 comprises a visual, printed or electronic outputs for local or remote monitoring of the patient P and/or the at least one room or environment 12. The information and data is output at block 32 as illustrated in FIG. 1 and ultimately displayed on a terminal 34, printed on a printer 36 and/or used to perform some other action 40, such as generating an audio or visual alarm 38. The actions 40 are a result of analyzing and comparing the information gathered in the inventory and data collection system 22. The actions 40 may include, but are not limited to the following:

Research (e.g., infection rates versus room air quality)
Air quality control
Room contamination evaluation and remediation
Air purifier monitoring
Air cleaning element quality
Air cleaning element reorder
Air cleaning element replacement
Air cleaning element cleaning
Room condition sensing
  Temperature
  Humidity
  Air quality
Record retention of air quality and room conditions
Alarm
Investigation of issues One important aspect of the system 10 and method found by the inventor is that the system 10 and method permit research to hopefully reduce infection rates in patients P. For example, the inventory and data collection system 22 or a user may find a correlation between patient infection rates in a particular room or environment 12 of a hospital and a particular type of clinical procedure. For example, during an open heart surgery or brain surgery for a patient P who obtained an infection it may be determined that during that procedure the temperature was higher than normal and with the ultraviolet output of the air purifier 14 being at an undesirable level or it may be determined that the condition of the air cleaning element 16 during that procedure had an undesirable amount of contamination, even though, for example, the air cleaning element was not due for replacement at the time.

Advantageously, the system 10 and method may provide a correlation between one or more clinical and physical data and parameters 18 and the physical data and parameters 19 associated with the at least one room or environment 12. Some other examples of the research can be investigating patterns of air contamination during a medical procedure, determining correlation between air quality and infection rates or other clinical outcomes, or evaluating the effectiveness of the system 10 and method for the at least one room or environment 12. The system 10 provides previously unknown means and apparatus for gathering and interpreting data.

Another advantageous feature of the system 10 and method is that it provides for ordering and/or automatic reordering of the air cleaning element 16 used in the air purifier 14 in response to at least one of the clinical and physical data and parameters 18 or the physical data and parameters 19 sensed or an evaluation of such information and data. Once the outputs 30 are generated, it may be determined that one or more actions 40 need to be taken and these actions 40 may be automated or manual. For example, the action of reordering the air cleaning element 16 for the air purifier 14 may be done either manually by a user or the system 10 may automatically generate a purchase order (not shown) which is submitted to an air cleaning element supplier in order to reorder and obtain a new air cleaning element 16 for the air purifier 14. Alternatively, it may be determined that the humidity or temperature needs to be raised or lowered in the at least one room or environment 12 for optimal care of the patient P and, most importantly, for reducing or eliminating unwanted airborne contamination in the at least one room or environment 12.

Referring now to FIG. 2, a schematic is shown of the system 10 illustrating one embodiment of a procedure or a methodology in accordance with one embodiment of the invention being described. The procedure or method starts at block 50 wherein the user inputs the clinical and physical data and parameters 18 into the inventory and data collection system 22 using the input means, such as the input terminal 20. The routine proceeds to block 52 wherein the physical data and parameters 19 described earlier herein are input or sensed and input into the inventory and data collection system 22.

At block 54, the routine proceeds with the inventory and data collection system 22 and/or the user evaluates and compares the clinical and physical data and parameters 18 and evaluates relationships between or among the clinical and physical data and parameters 18 and the physical data and parameters 19. At block 56, the output means 30 allows for the user to display, print, store, network or monitor the clinical and physical data and parameters 18. For example, the output means 30 may generate a visual report for display on the input terminal 20 or a printed report or form or other output for local or remote monitoring. Although not shown, the various data and information generated or received at blocks 50-57 may be stored on the server or storage means 28 mentioned earlier herein, but which is not shown in FIG. 2 for ease of illustration. At block 57, the clinical and physical data and parameters 18 and the physical data and parameters 19 are evaluated and compared before preceding to block 58. It is determined at decision block 58 whether any actions are required or necessary. If no actions are required or necessary, then the routine proceeds back to block 50 as shown.

If actions are necessary, as determined by the user or the inventory and data collection system 22, then one or more actions are performed at block 60. In this regard, the actions may include at least one or a plurality of the following:

Research (e.g., infection rates versus room air quality)
Air quality control
Room contamination evaluation and remediation
Air purifier monitoring
Air cleaning element quality
Air cleaning element reorder
Air cleaning element replacement
Air cleaning element cleaning
Room condition sensing
   Temperature
   Humidity
   Air quality
Record retention of air quality and room conditions
Alarm
Investigation of issues Although not shown, the inventory and data collection system 22 may comprise a microprocessor (not shown) programmed to control the operation of the inventory and data collection system 22 and to perform one or more of the actions mentioned earlier relative to block 60. The processor may have at least one or a plurality of lookup tables stored in suitable memory or storage means 28 that correlates predetermined conditions with the actions to be taken. The following table is illustrative of some of the correlations:

| INPUT OF SENSED INFORMATION BY USER INPUTS 24 OR SENSOR INPUTS 26 | ACTION(S) |
| --- | --- |
| Unreasonably high contamination sensed in operating room or environment 12 | Generate alarm 38, check air cleaning element 16, generate warning notice or alarm of unreasonably high contaminate level |
| At least one sensor 26 senses that air cleaning element 16 is either overloaded with contaminates or it is close to being over contaminated (e.g., it is anticipated that the air cleaning element 16 becomes overloaded during a surgical procedure) | Automatic reordering of air cleaning element 16 from supplier Replace air cleaning element 16 once received Alternatively, an automatic call to aservice technician to service the air purifier 14 |
| User compares contaminate particulate level from the physical data and parameters 19 to the patient's diagnosis and the type of clinical event time and determines that, again, the air cleaning element 16 needs to be replaced. | User orders and/or replaces air cleaning element 16 manually or contacts a technician to service the air purifier 14 in order to improve the air purity and quality in the at least one room or environment 12 |
| Evaluation of the air cleaning element 16 and any contamination level | If contamination is determined from the at least one of a comparison of the clinical and physical data and parameters 18 and the physical data and parameters 19, then the system 10 may generate through the output or output means 30 an audio or visual alarm 38 to replace the air cleaning element 16 or service the air purifier 14. |
| A clinical procedure is being performed or has been completed, with input of procedure information, via manual entry, networked data, or visual sensors which can detect a discrete procedure | A clinical event is logged in the system's 10 memory, a new single-procedure air cleaning element 16 is ordered or marked for order in a printed, displayed or transmitted manner. |
| A number of clinical procedures are being performed or have been completed, with input of procedure information, via manual entry, networked data, or visual sensors which can detect discrete procedures. | The clinical events, either grouped or individually, are logged in the system's 10 memory, a new multi-procedure air cleaning element 16 or group of single-procedure air cleaning elements 16 are ordered or marked for order in a printed, displayed, or transmitted manner. |

Advantageously, the system 10 and method provide the following advantages:
  Air purifier 14 service and/or replacement of air cleaning element 16.
  Automated reordering of a used air cleaning element 16.
  Improved air quality in the at least one room or environment 12.
  Decrease in the infection rates of patients P as a result of air contamination in the at least one room or environment 12.
  Providing an improved system 10 and method which is adapted to maintain an appropriate level of replacement air cleaning elements 16 and parts for the air purifier 14 in response to at least one of the clinical and physical data and parameters 18 or the physical data and parameters 19.
  Ability to track air quality in the at least one room or environment 12.
  Ability to track compliance with usage of the system 10.
  Ability to monitor the performance of the system 10, either locally or remotely.
  Evaluation of clinical and physical data for a room, such as an operating room, to provide a whole picture.

The system 10 and air purifier 14 with air cleaning element 16 may be used in an operating room or other room to reduce infectious biological debris from spreading contamination to the patient P or from one procedure for a first patient P to a second patient P during another procedure. In other words, the system 10 and method reduce the spread of contamination by enabling a user to understand the source of the contamination using the physical data and parameters 19 and also improving the efficiency of the air purifier 14 by, for example, replacing or cleaning of the air cleaning element 16. As mentioned earlier herein, this air cleaning element reordering and/or replacement may be preemptive or at a time when normal circumstances would suggest to the user that an air cleaning element replacement is not necessary.

The embodiments being described provide a system 10 and method for purifying operating room air which allows each surgical procedure to have a non-contaminated air purifier 14 to prevent the spread of bacterial contamination. Thus, for example, if the at least one sensor 26 associated with the air purifier 14 senses any contamination of the air cleaning element 16, then the system 10 and/or an inventory and data collection system (IDCS) 22 may call for an immediate replacement of the air cleaning element 16, even if it does not have many hours of use. Alternatively, it is also contemplated that the system 10 and method could cause a notification, reorder and replacement of an air cleaning element 16 if, for example, the contamination of the air cleaning element 16 is sensed to be greater than 1.5 in $H_2O$ internal air pressure which can be done by three illustrative ways: a predetermined elapse of time since the air cleaning element 16 was last changed, increased pressure inside the system 10 via the pressure sensor mentioned earlier, or increases of air contamination in the at least one room or environment 12 indicating that adequate cleaning is not being performed.

One feature, as mentioned in earlier herein, could be a camera C (FIG. 1) built into the system 10 which would detect clinical events, such as surgeries. An algorithm or artificial intelligence is store in memory of the inventory and data collection system (IDCS) 22 to determine when a procedure has been completed, and this information could be incorporated into the database for usage tracking/ordering of the air cleaning element 16 and the like. This could also be used to determine the number of occupants in the at least one room or environment 12, which is important in evaluating air quality.

The at least one sensor 26 may also comprise another sensor which could be added to the system 10 is an external air pressure sensor (not shown). This would measure the number of time the door D in an operating room (which is slightly pressurized) has opened. This is an important data input in evaluating air quality.

An internal air pressure sensor which could be used to determine abnormalities in the function of the system 10. Readings too high could indicate an obstructed outflow, too low inflow, etc. Again this would be incorporated into the logging/transmitting/alarming process.

One embodiment of the invention may comprise a system for maintaining or monitoring at least one environment having at least one air purifier, the system comprising at least one first input or input means for a user to input at least one of clinical data or physical parameters into a collection system, at least one second input or sensor associated with the environment for collecting physical data regarding the environment and for inputting it into the collection system, at least one output for outputting the at least one of clinical or physical parameters and the physical data, at least one element that uses and processes the at least one of clinical or physical parameters and the physical data in a predetermined format as input from the at least one first input and the at least one second input, respectively, and outputs integrated information, and the system being adapted to permit a user to use such integrated information to at least one of maintain or improve the at least one of the environment or take at least one action in response to the integrated information, the integrated information being adapted or used for at least one of research, improving air quality, quality review of the environment or control or notification of at least one issue associated with the environment or the integrated information.

Another embodiment of the invention may comprise a system for improving air quality in at least one hospital room or operating room, the system comprising at least one first input or sensor for inputting for a user to input at least one of clinical data or physical parameters into a collection system, at least one second input or sensor associated with an environment for collecting physical data regarding the environment and for inputting it into the collection system, at least one output for outputting the at least one of clinical or physical parameters and the physical data, at least one element that uses and processes the at least one of clinical or physical parameters and the physical data as input from the at least one first input and the at least one second input, respectively, and outputs integrated information, and the system being adapted to permit use of such integrated information to take at least one action that at least one of maintains or improves the air quality.

Another embodiment of the invention may comprise a method for maintaining or monitoring at least one environment having at least one air purifier, the method comprising the steps of inputting at least one clinical data or physical parameters into a collection system, sensing physical data regarding the at least one environment and for inputting it into the collection system, outputting from the collection system at least one output generated using the at least one of clinical or physical parameters and the physical data, using at least one element to process the at least one of clinical or physical parameters and the physical data as input from at least one first input and at least one second input, respectively, and outputs integrated information in response thereto, and using such integrated information to at least one of maintain or improve the at least one of the environment or take at least one action in response to the integrated information, the integrated information being adapted or used for at least one of research, improving air quality, quality review of the environment or control or notification of at least one issue associated with the environment or the integrated information.

Still another embodiment of the invention may comprise an inventory system for supporting the purifying of operating room air on a per-patient basis consisting of a record of patient identifying information, a record describing an air cleaning element utilized in an air purifier located in an operating room, the air cleaning element being used for an individual patient procedure, the record describing the air cleaning element comprising manufacturer name, part number, and/or serial number in association with the patient identifying information, the inventory system adapted to facilitate inventory actions such as re-ordering, replacement, recordkeeping, invoicing and/or billing of the air cleaning element, the inventory system associating the inventory actions to the patient identifying information.

Still another embodiment of the invention may comprise a method of purifying operating room air comprising activating a portable air purifier, after a surgical procedure, removing a contaminated air cleaning element from the air purifier, recording data regarding the air cleaning element to effect remuneration or recordkeeping by hospital, air cleaning element manufacturer, patient, or related payor in electronic or paper medical record or related document, replacing the air cleaning element with new air cleaning element.

Another embodiment of the invention may comprise a method of purifying operating room air comprising locating an area of an operating room which has the highest amount of human traffic/and or airborne contamination, positioning an air purifier proximate to the area, the air purifier having an air cleaning element, after a surgical procedure, removing a contaminated air cleaning element from the air purifier, recording data regarding the air cleaning element to effect remuneration or recordkeeping by hospital, air cleaning element manufacturer, patient, or related payor in electronic or paper medical record or related document, replacing the air cleaning element with new air cleaning element.

Another embodiment of the invention may comprise a method of purifying operating room air comprising positioning an air purifier adjacent to an operating room door, instrument table or patient table, the air purifier having an air cleaning element, after a surgical procedure, removing a contaminated air cleaning element from the air purifier, recording data regarding the air cleaning element to effect remuneration or recordkeeping by hospital, air cleaning element manufacturer, patient, or related payor in electronic or paper medical record or related document, replacing the air cleaning element with new air cleaning element.

Another embodiment of the invention may comprise a method of purifying operating room air comprising placing an air purifier, the air purifier having means for direct bacterial deactivation, such as irradiation, chemical oxidation, or ionization, and an air cleaning element, after a surgical procedure, removing a contaminated air cleaning element from the air purifier, recording data regarding the air cleaning element to effect remuneration or recordkeeping by hospital, air cleaning element manufacturer, patient, or related payor in electronic or paper medical record or related document, replacing the air cleaning element with new air cleaning element.

Another embodiment of the invention may comprise a method of purifying operating room air comprising placing an air purifier, the air purifier having means for air quality monitoring and an air cleaning element, after a surgical procedure, removing a contaminated air cleaning element from the air purifier, recording data regarding the air cleaning element to effect remuneration or recordkeeping by hospital, air cleaning element manufacturer, patient, or related payor in electronic or paper medical record or related document, recording data regarding air quality information in a patient record or related record, replacing the air cleaning element with new air cleaning element.

Another embodiment of the invention may comprise a method for providing an air purifier for operating room use the purifier provided to the hospital or surgical facility at no cost or for materially less than the typical purchase cost of comparable product, the purifier containing an interchangeable air cleaning element, the air cleaning element changed on a per patient basis, the hospital or surgical facility, patient, payor or related party, paying for the air cleaning element on a per-patient basis, revenue from the air cleaning element usage offsetting cost of the purifier.

Another embodiment of the invention may comprise an inventory and data collection system, operative with an air purification device, for the purpose of recording and integration of data regarding physical parameters and clinical parameters within a clinical situation.

Advantageously, the embodiments shown and described herein could be used alone or together and/or in combination with one or more of the features covered by one or more of the claims set forth herein, including but not limited to one or more of the features or steps mentioned in the Summary of the Invention and the claims.

While the system, apparatus and method herein described constitute preferred embodiments of this invention, it is to be understood that the invention is not limited to this precise system, apparatus and method, and that changes may be made therein without departing from the scope of the invention which is defined in the appended claims.

What is claimed is:

1. A system for maintaining or monitoring at least one environment having at least one air purifier, said system comprising:
    at least one first input or input means for a user to input at least one of clinical data or physical parameters into a collection system;
    at least one second input or sensor associated with said environment for collecting physical data regarding the environment and for inputting it into said collection system;
    at least one output for outputting said at least one of clinical or physical parameters and said physical data;
    at least one element that uses and processes said at least one of clinical or physical parameters and said physical data in a predetermined format as input from said at least one first input and said at least one second input, respectively, and outputs integrated information; and
    said system being adapted to permit a user to use such integrated information to at least one of maintain or improve said at least one of said environment or take at least one action in response to said integrated information;
    said integrated information being adapted or used for at least one of research, improving air quality, quality review of said environment or control or notification of at least one issue associated with said environment or said integrated information.

2. The system as recited in claim 1 wherein said at least one action is a service of said air purifier.

3. The system as recited in claim 2 wherein said service is changing an air cleaning element in said air purifier.

4. The system as recited in claim 1 wherein said at least one action is automatically controlling operation of said air purifier in said at least one environment in response to said integrated information.

5. The system as recited in claim 1 wherein said at least one action is using said integrated information for at least one of research, evaluation of air particulate levels, or providing a condition of said at least one environment.

6. The system as recited in claim 5 wherein said condition of said at least one environment is at least one of air particulate level, contamination level, cleanliness, temperature, humidity or air quality.

7. The system as recited in claim 1 wherein said at least one environment is a room where a patient is located.

8. The system as recited in claim 1 wherein said at least one environment is an operating room.

9. The system as recited in claim 1 wherein said clinical data is at least one of patient information and/or identification codes, diagnosis, location identification, clinical event type, clinical event length or clinical event time.

10. The system as recited in claim 1 wherein said physical data is at least one of air particulate levels, air quality, temperature, humidity, air purifier functionality, ultraviolet output, air cleaning element condition, air cleaning element identification codes or air purifier identification codes.

11. The system as recited in claim 1 wherein said at least one action includes at least one of research, air quality control, room contamination evaluation and remediation, air purifier monitoring, air cleaning element quality, air cleaning element reorder, air cleaning element replacement, air cleaning element cleaning, room condition sensing temperature, humidity and/or air quality, record retention of air quality and room conditions, alarm and/or investigation of issues.

12. The system as recited in claim 1 wherein said at least one sensor comprises at least one of an air particle sensor, an optical sensor, an internal pressure sensor, a humidity sensory and/or a temperature sensor.

13. The system as recited in claim 1 wherein said air cleaning element may be one of a filter, an electrostatic screen, an ultraviolet light or the like.

14. A system for improving air quality in at least one hospital room or operating room, said system comprising:
  at least one first input or sensor for inputting for a user to input at least one of clinical data or physical parameters into a collection system;
  at least one second input or sensor associated with an environment for collecting physical data regarding said environment and for inputting it into said collection system;
  at least one output for outputting said at least one of clinical or physical parameters and said physical data;
  at least one element that uses and processes said at least one of clinical or physical parameters and said physical data as input from said at least one first input and said at least one second input, respectively, and outputs integrated information; and
  said system being adapted to permit use of such integrated information to take at least one action that at least one of maintains or improves the air quality.

15. The system as recited in claim 14 wherein said at least one action is a service of an air purifier.

16. The system as recited in claim 15 wherein said service is re-ordering a replacement air cleaning element for said air purifier.

17. The system as recited in claim 15 wherein said service is changing an air cleaning element in said air purifier.

18. The system as recited in claim 14 wherein said at least one action is automatically controlling operation of an air purifier in said at least one hospital room or operating room in response to said integrated information.

19. The system as recited in claim 14 wherein said at least one action is using said integrated information for at least one of research, evaluation of air particulate levels, or providing a condition of said at least one hospital room or operating room.

20. The system as recited in claim 19 wherein said condition of said at least one hospital room or operating room is at least one of air particulate level, contamination level, cleanliness, temperature, humidity or air quality.

21. The system as recited in claim 14 wherein said clinical data is at least one of patient information and/or identification codes, diagnosis, location identification, clinical event type, clinical event length or clinical event time.

22. The system as recited in claim 14 wherein said physical data is at least one of air particulate levels, air quality, temperature, humidity, air purifier functionality, ultraviolet output, air cleaning element condition, air cleaning element identification codes or air purifier identification codes.

23. The system as recited in claim 14 wherein said at least one action includes at least one of research, air quality control, room contamination evaluation and remediation, air purifier monitoring, air cleaning element quality, air cleaning element reorder, air cleaning element replacement, air cleaning element cleaning, room condition sensing temperature, humidity and/or air quality, record retention of air quality and room conditions, alarm and/or investigation of issues.

24. A method for maintaining or monitoring at least one environment having at least one air purifier, said method comprising the steps of:
  inputting at least one clinical data or physical parameters into a collection system;
  sensing physical data regarding the at least one environment and for inputting it into said collection system;
  outputting from said collection system at least one output generated using said at least one of clinical or physical parameters and said physical data;
  using at least one element to process said at least one of clinical or physical parameters and said physical data as input from at least one first input and at least one second input, respectively, and outputs integrated information in response thereto; and
  using such integrated information to at least one of maintain or improve said at least one of said environment or take at least one action in response to said integrated information;
  said integrated information being adapted or used for at least one of research, improving air quality, quality review of said environment or control or notification of at least one issue associated with said environment or said integrated information.

25. The method as recited in claim 24 wherein said at least one action is a service of said air purifier.

26. The method as recited in claim 25 wherein said method comprises the step of changing an air cleaning element in said air purifier in response to said integrated information.

27. The method as recited in claim 24 wherein said method further comprises the step of:
  automatically controlling operation of said air purifier in said at least one environment in response to said integrated information.

28. The method as recited in claim 24 wherein said method further comprises the step of:
using said integrated information for at least one of research, evaluation of air particulate levels, or providing a condition of said at least one environment.

29. The method as recited in claim 28 wherein said condition of said at least one environment is at least one of air particulate level, contamination level, cleanliness, temperature, humidity or air quality.

30. The method as recited in claim 24 wherein said at least one environment is a room where a patient is located.

31. The method as recited in claim 24 wherein said at least one environment is an operating room.

32. The method as recited in claim 24 wherein said clinical data is at least one of patient information and/or identification codes, diagnosis, location identification, clinical event type, clinical event length or clinical event time.

33. The method as recited in claim 24 wherein said physical data is at least one of air particulate levels, air quality, temperature, humidity, air purifier functionality, ultraviolet output, air cleaning element condition, air cleaning element identification codes or air purifier identification codes.

34. An inventory system for supporting the purifying of operating room air on a per-patient basis consisting of:
a record of patient identifying information;
a record describing an air cleaning element utilized in an air purifier located in an operating room, said air cleaning element being used for an individual patient procedure;
said record describing said air cleaning element comprising manufacturer name, part number, and/or serial number in association with said patient identifying information;
said inventory system adapted to facilitate inventory actions such as re-ordering, replacement, recordkeeping, invoicing and/or billing of said air cleaning element;
said inventory system associating said inventory actions to said patient identifying information.

35. A method of purifying operating room air comprising:
activating a portable air purifier;
after a surgical procedure, removing a contaminated air cleaning element from said air purifier;
recording data regarding said air cleaning element to effect remuneration or recordkeeping by hospital, air cleaning element manufacturer, patient, or related payor in electronic or paper medical record or related document;
replacing said air cleaning element with new air cleaning element.

36. A method of purifying operating room air comprising:
locating an area of an operating room which has the highest amount of human traffic/and or airborne contamination;
positioning an air purifier proximate to said area, said air purifier having an air cleaning element;
after a surgical procedure, removing a contaminated air cleaning element from said air purifier;
recording data regarding said air cleaning element to effect remuneration or recordkeeping by hospital, air cleaning element manufacturer, patient, or related payor in electronic or paper medical record or related document;
replacing said air cleaning element with new air cleaning element.

37. A method of purifying operating room air comprising:
positioning an air purifier adjacent to an operating room door, instrument table or patient table, said air purifier having an air cleaning element;
after a surgical procedure, removing a contaminated air cleaning element from said air purifier;
recording data regarding said air cleaning element to effect remuneration or recordkeeping by hospital, air cleaning element manufacturer, patient, or related payor in electronic or paper medical record or related document;
replacing said air cleaning element with new air cleaning element.

38. A method of purifying operating room air comprising:
placing an air purifier, said air purifier having means for direct bacterial deactivation, such as irradiation, chemical oxidation, or ionization, and an air cleaning element;
after a surgical procedure, removing a contaminated air cleaning element from said air purifier;
recording data regarding said air cleaning element to effect remuneration or recordkeeping by hospital, air cleaning element manufacturer, patient, or related payor in electronic or paper medical record or related document;
replacing said air cleaning element with new air cleaning element.

39. A method of purifying operating room air comprising:
placing an air purifier, said air purifier having means for air quality monitoring and an air cleaning element;
after a surgical procedure, removing a contaminated air cleaning element from said air purifier;
recording data regarding said air cleaning element to effect remuneration or recordkeeping by hospital, air cleaning element manufacturer, patient, or related payor in electronic or paper medical record or related document;
recording data regarding air quality information in a patient record or related record;
replacing said air cleaning element with new air cleaning element.

40. A method for providing an air purifier for operating room use:
said purifier provided to the hospital or surgical facility at no cost or for materially less than the typical purchase cost of comparable product;
said purifier containing an interchangeable air cleaning element;
said air cleaning element changed on a per patient basis;
said hospital or surgical facility, patient, payor or related party, paying for said air cleaning element on a per-patient basis;
revenue from said air cleaning element usage offsetting cost of said purifier.

41. An inventory and data collection system, operative with an air purification device, for the purpose of recording and integration of data regarding physical parameters and clinical parameters within a clinical situation.

42. The inventory and data collection system of claim 41 wherein said clinical situation is a surgical procedure.

43. The inventory and data collection system of claim 41 wherein said clinical parameters include at least one of patient information and/or identification codes, diagnosis, location identification, clinical event type, clinical event length, clinical event time.

44. The inventory and data collection system of claim 41 wherein said physical parameters include at least one of air particulate levels, air quality, temperature, humidity, air purifier functionality, ultraviolet output, air cleaning element condition, air cleaning element identification codes or air purifier identification codes.

45. The inventory and data collection system of claim 41 wherein said integration comprises a means to record and/or display said clinical and physical parameters substantially contemporaneously to allow for a user to readily evaluate the relationship between said parameters.

46. The inventory and data collection system of claim 41 wherein said system incorporates an input means to allow for automatic and/or user input of said clinical and physical parameters;
   said input means incorporating at least one of sensors, keyboard, touchscreen, remote signal, radiofrequency identification, or similar means.

47. The inventory and data collection system of claim 41 wherein said system incorporates an output means to allow for user monitoring of said clinical and physical parameters;
   said output means consisting of visual, printed, or electronic outputs for local or remote monitoring.

48. The inventory and data collection system of claim 41 wherein said system incorporates a storage means to allow for storage of said clinical and physical parameters;
   said storage means consisting of magnetic, solid state, cloud, or other equivalent data storage methodologies operating at a local or remote location.

* * * * *